(12) United States Patent
Hane

(10) Patent No.: US 12,161,801 B2
(45) Date of Patent: Dec. 10, 2024

(54) RESPIRATORY BLOWING DEVICE

(71) Applicant: Murata Manufacturing Co., Ltd., Kyoto (JP)

(72) Inventor: Yoshitaka Hane, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 534 days.

(21) Appl. No.: 17/646,310

(22) Filed: Dec. 29, 2021

(65) Prior Publication Data

US 2022/0118203 A1 Apr. 21, 2022

Related U.S. Application Data

(63) Continuation of application No. PCT/JP2020/018518, filed on May 7, 2020.

(30) Foreign Application Priority Data

Jul. 4, 2019 (JP) .................................. 2019-125288

(51) Int. Cl.
*A61M 16/00* (2006.01)
*F04D 25/08* (2006.01)
(Continued)

(52) U.S. Cl.
CPC ......... *A61M 16/0066* (2013.01); *F04D 25/08* (2013.01); *F04D 29/403* (2013.01);
(Continued)

(58) Field of Classification Search
CPC ...... F04D 25/08; F04D 29/403; F04D 29/661; F04D 29/4213; F04D 29/705;
(Continued)

(56) References Cited

U.S. PATENT DOCUMENTS 4,715,998 A * 12/1987 Clow .................... A61M 16/16
                                                                      261/142
5,228,107 A * 7/1993 Marino ................... F24F 6/025
                                                                      392/394
(Continued)

FOREIGN PATENT DOCUMENTS

JP    2008-517682 A    5/2008
JP    2009-508647 A    3/2009

OTHER PUBLICATIONS

International Search Report issued in Application No. PCT/JP2020/018518, dated Jul. 7, 2020.

*Primary Examiner* — Brian P Wolcott
(74) *Attorney, Agent, or Firm* — Pearne & Gordon LLP

(57) ABSTRACT

The respiratory blowing device is provided with a first unit including a first housing and a second unit including a rotating body and a second housing. The first housing includes a first outlet, the rotating body includes a first coupling port and a first coupling path, and the second housing includes a first inlet and a second outlet. The rotating body is configured to rotate between a first position and a second position. At the first position, the first outlet is coupled to the first coupling port in a state that the first housing and the second housing are separated from each other. At the second position, the first housing is attached to the second housing by the rotation of the first housing to approach the second housing in a state that the first outlet is coupled to the first coupling port.

20 Claims, 7 Drawing Sheets

(51) Int. Cl.
  *F04D 29/40* (2006.01)
  *F04D 29/66* (2006.01)
  *F04B 43/04* (2006.01)

(52) U.S. Cl.
  CPC ....... *F04D 29/661* (2013.01); *A61M 2205/42* (2013.01); *F04B 43/046* (2013.01)

(58) Field of Classification Search
  CPC .. A61M 16/00; A61M 16/0066; A61M 16/16; A61M 16/109; A61M 16/161; A61M 2205/42; A61M 2205/3368; A61M 2209/086; F24F 6/02–16
  See application file for complete search history.

(56) References Cited

U.S. PATENT DOCUMENTS

| | | | | |
|---|---|---|---|---|
| 6,256,454 | B1* | 7/2001 | Dykes | A61G 11/00 392/403 |
| 6,663,695 | B2* | 12/2003 | Ike | B01D 46/521 95/71 |
| 9,038,629 | B2* | 5/2015 | Smith | A61M 16/0066 128/203.16 |
| 9,656,034 | B2* | 5/2017 | Kepler | A61M 16/0069 |
| 10,980,966 | B2* | 4/2021 | DiMatteo | A61M 16/1045 |
| 11,833,300 | B2* | 12/2023 | Higashiyama | A61M 16/0066 |
| 2007/0169776 | A1 | 7/2007 | Kepler et al. | |
| 2008/0000474 | A1* | 1/2008 | Jochle | A61M 16/0858 128/204.22 |
| 2017/0203064 | A1* | 7/2017 | Suzuki | A61M 16/107 |
| 2018/0110946 | A1* | 4/2018 | Palou Fustè | A61M 16/06 |
| 2020/0101258 | A1* | 4/2020 | Dimatteo | A61M 16/162 |

\* cited by examiner

RESPIRATORY BLOWING DEVICE

CROSS REFERENCE TO RELATED APPLICATION

This is a continuation of International Application No. PCT/JP2020/018518 filed on May 7, 2020 which claims priority from Japanese Patent Application No. 2019-125288 filed on Jul. 4, 2019. The contents of these applications are incorporated herein by reference in their entireties.

BACKGROUND ART

Technical Field

The present disclosure relates to a respiratory blowing device.

The cause of sleep apnea syndrome in which breathing is stopped during sleep is considered that the respiratory passage through which air passes becomes physically narrow. As an effective treatment for sleep apnea syndrome, there is a treatment using a CPAP device.

The CPAP device continuously sends air to widen the respiratory passage in order to prevent apnea during sleep. The CPAP device includes a blower unit including a blower inside the device. The CPAP device is configured such that air sucked into the device is sent to a mask worn on the nose or mouth of a user via a hose (air tube) for air transport.

In this CPAP device, as disclosed in Japanese Unexamined Patent Application Publication (Translation of PCT Application) No. 2009-508647 (Patent Document 1), there is a case that a blower unit (first unit) and a humidification unit (second unit) are connected and used.

In the CPAP device disclosed in Patent Document 1, a blower unit and a humidification unit are connected to each other using a coupling assembly. The coupling assembly includes a base portion forming a horizontal plane, and a side wall structure provided at one end of the base portion. The side wall structure is provided with a first coupling port to which the blower unit is coupled, a second coupling port to which the humidification unit is coupled, and a flow path to couple the first coupling port and the second coupling port. The first coupling port and the second coupling port are arranged side by side.

When the blower unit is coupled to the first coupling port, the air outlet of the blower unit is inserted into the first coupling port in an insertion direction parallel to the horizontal direction. Similarly, when the humidification unit is coupled to the second coupling port, the air inlet of the humidification unit is inserted into the second coupling port in a direction parallel to the insertion direction of the blower unit.

Patent Document 1: Japanese Unexamined Patent Application Publication (Translation of PCT Application) No. 2009-508647

BRIEF SUMMARY

In the CPAP device disclosed in Patent Document 1, it is necessary to insert the blower unit into the first coupling port by holding the blower unit with one hand in a state that the side wall structure of the coupling assembly is held with the other hand. With this, it is not easy to intuitively understand how much force and distance are required when inserting the blower unit. As a result, when the insertion of the blower unit is not sufficient, the coupling state between the blower unit and the first coupling port is unstable. The same phenomenon may occur in the humidification unit.

Such a situation may also occur when the blower unit and the humidification unit are directly inserted and assembled.

The present disclosure provides a respiratory blowing device including a first unit and a second unit and is capable of reliably coupling the first unit and the second unit.

A respiratory blowing device according to the present disclosure includes a first unit including a blower and a first housing that houses the blower, and a second unit including a rotating body to which the first unit is detachably coupled and a second housing that rotatably supports the rotating body. The first housing is capable of being attached to the second housing. The first housing includes a first outlet for discharging air to the outside of the first housing. The rotating body includes a first coupling port to which the first outlet is detachably coupled in a direction intersecting a rotation axis of the rotating body, and a first coupling path communicating with the first coupling port. The second housing includes a first inlet capable of being coupled to the first coupling path and to which air is introduced from the first coupling path, and a second outlet for discharging air introduced from the first inlet to the outside of the second housing. The rotating body is configured to rotate between a first position and a second position. In the first position, the first outlet is coupled to the first coupling port in a state that the first housing and the second housing are separated from each other. In the second position, the first housing is attached to the second housing by the rotation of the first housing to approach the second housing in a state that the first outlet is coupled to the first coupling port.

In the respiratory blowing device according to the present disclosure, the second housing can be provided with an ancillary portion that assists the attachment of the first housing to the second housing when the rotating body moves to the second position in the state that the first outlet is coupled to the first coupling port.

In the respiratory blowing device according to the present disclosure, the ancillary portion can be provided with an engaging portion that engages with the first housing in a state that the first housing is attached to the second housing.

In the respiratory blowing device according to the present disclosure, the second housing may have an attachment surface that faces vertically upward and to which the first housing is attached. The vertically upward is a direction perpendicular to the main bottom surface of the second housing. In this case, the rotation axis of the rotating body can be parallel to the attachment surface, and the first coupling port of the rotating body can face upward in the first position.

In the respiratory blowing device according to the present disclosure, the rotating body may be configured to rotate to the second position by the own weight of the first unit in the state that the first outlet is coupled to the first coupling port in the first position.

In the respiratory blowing device according to the present disclosure, the rotating body can include a first terminal, and the first housing can include a second terminal capable of being coupled to the first terminal. Further, the second terminal can be coupled to the first terminal in the state that the first outlet is coupled to the first coupling port.

In the respiratory blowing device according to the present disclosure, the first housing may include a second inlet for introducing air from the outside of the first housing, and a first flow path that connects the second inlet and the first outlet and is provided with the blower. The second housing may include a third inlet for introducing air from the outside of the second housing, a third outlet for discharging air introduced from the third inlet to the outside of the second housing, and a second flow path connecting the third inlet and the third outlet. In this case, a silencer can be provided in the second flow path, and the rotating body includes a second coupling port to which the second inlet is detachably coupled and a second coupling path communicating with the second coupling port. The third outlet can be provided to be capable of being coupled to the second coupling path.

The respiratory blowing device according to the present disclosure can further include a damper that buffers an impact when the rotating body to which the first unit is coupled moves from the first position to the second position.

According to the present disclosure, it is possible to provide a respiratory blowing device including a first unit and a second unit and being capable of reliably coupling the first unit and the second unit.

DETAILED DESCRIPTION

Figure 1:
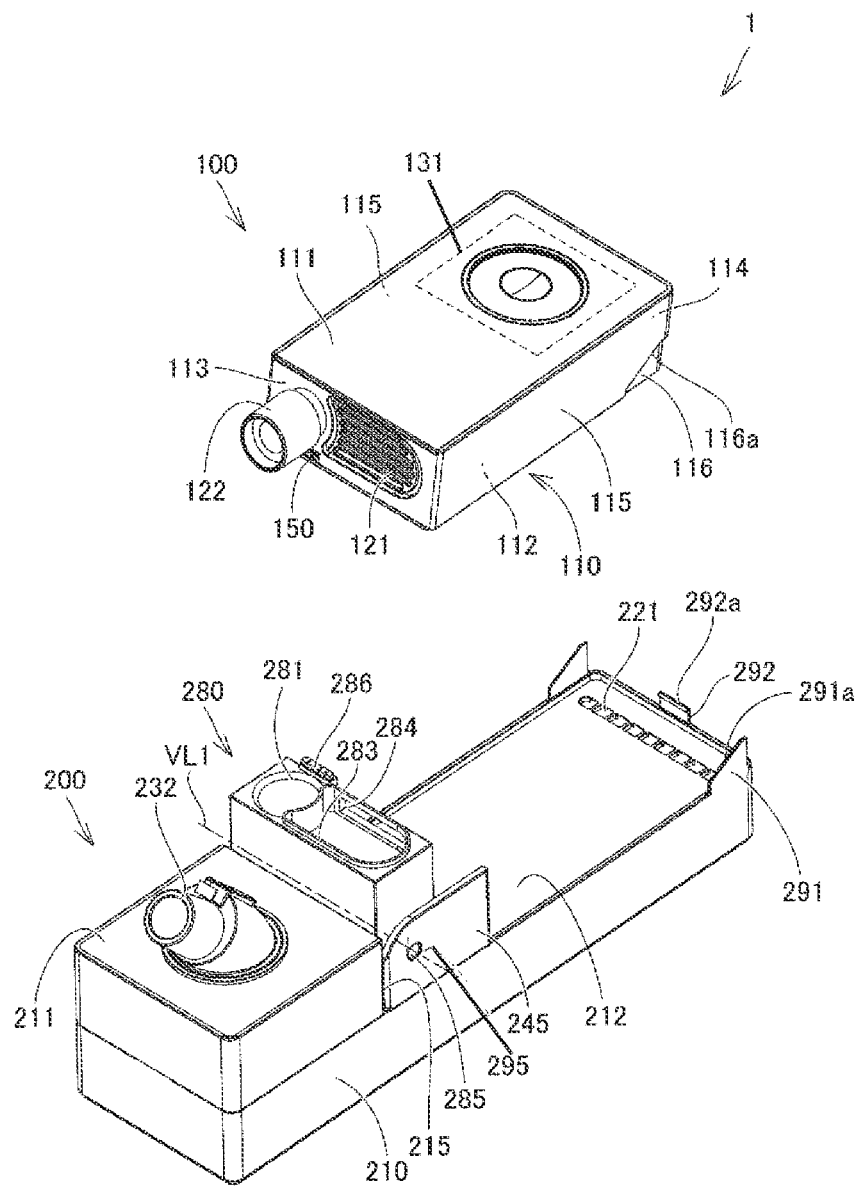
FIG. 1 is a perspective view of a CPAP device according to Embodiment 1 illustrating a state that a base unit and a main unit are separated from each other.

Hereinafter, embodiments of the present disclosure will be described in detail with reference to the drawings. The embodiments described below exemplify a case that the present disclosure is applied to a CPAP device as a respiratory blowing device. In the embodiments described below, the same or common portions are denoted by the same reference signs in the drawings, and the description thereof will not be repeated.

Embodiment 1

Figure 2:
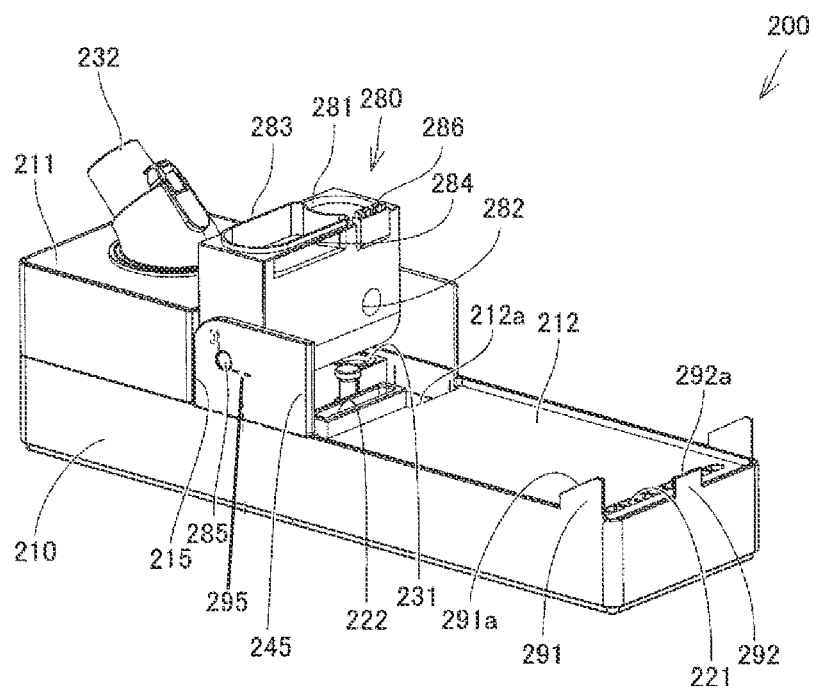
FIG. 2 is a perspective view of the base unit according to Embodiment 1 when viewed from the rear side.
Figure 3:
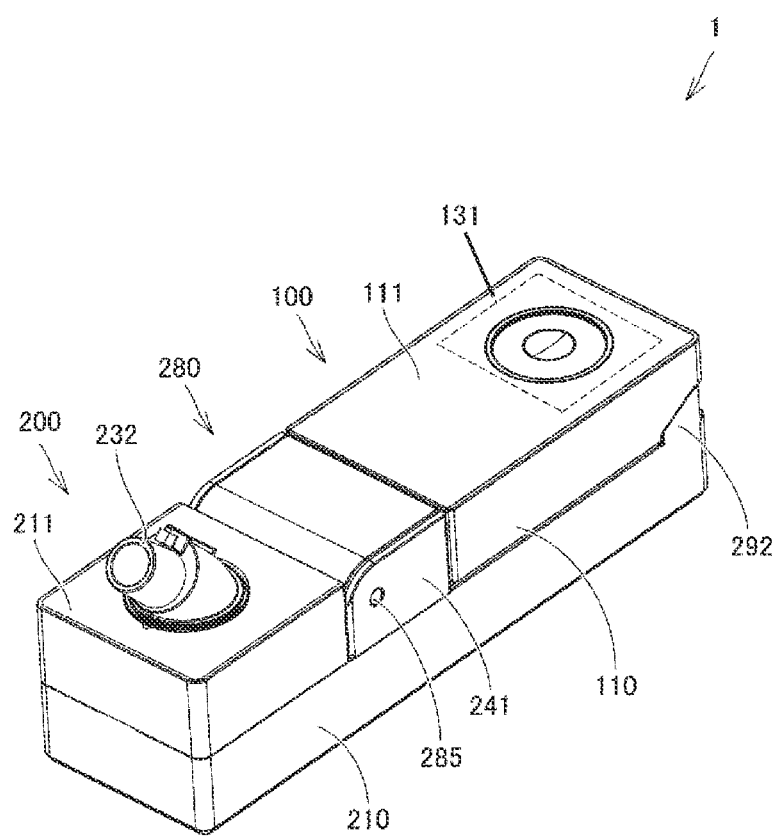
FIG. 3 is a perspective view of the CPAP device according to Embodiment 1 illustrating a state that the main unit is installed to the base unit.

FIG. 1 is a perspective view of a CPAP device according to Embodiment 1 illustrating a state that a base unit and a main unit are separated from each other. FIG. 2 is a perspective view of the base unit according to Embodiment 1 when viewed from the rear side. FIG. 3 is a perspective view of the CPAP device according to Embodiment 1 illustrating a state that the main unit is installed to the base unit. A CPAP device 1 according to Embodiment 1 will be described with reference to FIG. 1 to FIG. 3.

As illustrated in FIG. 1 to FIG. 3, the CPAP device 1 includes a main unit 100 as a first unit and a base unit 200 as a second unit. The main unit 100 mainly includes a blower 140 (see FIG. 6). The base unit 200 mainly includes a rotating body 280 and a humidification mechanism. The main unit 100 may be attached to and detached from the base unit 200.

Here, the CPAP device 1 is configured to be used in two states. In one state, the base unit 200 is attached to the main unit 100, and in the other state, the base unit 200 is not attached to the main unit 100.

More specifically, in the first use state that the CPAP device 1 is used with the base unit 200 being attached to the main unit 100, both of the main unit 100 and the base unit 200 are used; and in the second use state that the CPAP device 1 is used with the base unit 200 not being attached to the main unit 100, the main unit 100 is used but the base unit 200 is not used.

The CPAP device 1 is configured to have a plurality of units to be divided, and the units are configured to be attached to and detached from each other. This is because the configuration makes it possible to increase convenience not only at home but also away from home. That is, at home or the like, the CPAP device 1 may be used in the first use state described above by attaching the main unit 100 to the base unit 200. At the time away from home or the like, the CPAP device 1 may be used in the second use state described above without necessarily attaching the main unit 100 to the base unit 200.

The CPAP device 1 according to Embodiment 1 is provided with a cutout portion described later at a predetermined position of the base unit 200. The base unit 200 is attached to the main unit 100 such that the main unit 100 is disposed to be fitted into the cutout portion by using the rotating body 280 described later.

The main unit 100 includes a first housing 110 having a flat, substantially rectangular parallelepiped outer shape. The blower 140 (see FIG. 6) is housed inside the first housing 110. The first housing 110 is provided such that the first housing 110 may be attached to a second housing 210 of the base unit 200.

The first housing 110 includes an upper surface 111 and a lower surface 112 that are positioned side by side in the vertical direction in the use state, a front surface 113 and a rear surface 114, and a pair of side surfaces 115.

An operation portion 131 is provided on the upper surface 111 of the first housing 110. The lower surface 112 of the first housing 110 faces an attachment surface 212 of the second housing 210 in the first use state. The lower surface 112 of the first housing 110 is placed on the surface of a floor, a table, or the like in the second use state.

The front surface 113 of the first housing 110 is provided with a second inlet 121 for introducing air from the outside of the first housing 110, and a first outlet 122 for discharging air to the outside of the first housing 110. The second inlet 121 and the first outlet 122 are arranged side by side.

The first outlet 122 has a cylindrical shape. The first outlet 122 is provided to protrude forward from the front surface 113. The first outlet 122 is provided to be capable of being coupled to a first coupling port 281 of the rotating body 280 described later. The second inlet 121 is provided to be capable of being coupled to a second coupling port 283 of the rotating body 280 described later.

The pair of side surfaces 115 connects the upper surface 111 and the lower surface 112, and connects the front surface 113 and the rear surface 114. Cutout portions 116 are provided at the rear lower portions of the pair of side surfaces 115. The cutout portion 116 is provided with an inclined portion 116a that is inclined to the lower surface 112 toward the side of the front surface 113.

The first housing 110 has a second terminal 150. The second terminal 150 is provided on the front surface 113 of the first housing 110. The second terminal 150 is electrically connected to electronic components such as a controller 130 disposed in the first housing 110. The second terminal 150 is provided to be capable of being coupled to a first terminal 286 of the rotating body 280 described later.

The base unit 200 includes the rotating body 280 and the second housing 210. The second housing 210 has an outer shape of an elongated substantially rectangular parallelepiped shape having a cutout portion in a portion thereof in the longitudinal direction. The longitudinal direction of the second housing 210 is parallel to the front-rear direction of the second housing 210, and the cutout portion is provided at the rear portion side of the second housing 210.

The second housing 210 has an upper surface 211 and a lower surface that are positioned side by side in the vertical direction in the use state, and four side peripheral surfaces that connect the upper surface 211 and the lower surface; and the above-described cutout portion is provided at the upper surface side of the side peripheral surfaces. With this, the second housing 210 has a step-like shape in which a step portion 215 is provided on the upper surface side thereof. The lower surface of the second housing 210 is placed on the surface of a floor, a table, or the like in the first use state described later.

The second housing 210 includes a first inlet 231 capable of being coupled to a first coupling path 282 of the rotating body 280 described later and to which air is introduced from the first coupling path 282, and a second outlet 232 for discharging the air introduced from the first inlet 231 to the outside of the second housing 210.

The second housing 210 includes a third inlet 221 for introducing air from the outside of the second housing 210, a third outlet 222 for discharging the air introduced from the third inlet 221 to the outside of the second housing, and a second flow path 220 (see FIG. 6) connecting the third inlet 221 and the third outlet 222.

A portion of the upper surface 211 of the second housing 210 corresponding to the above-described cutout portion forms the attachment surface 212 to which the first housing 110 is attached in the first use state. The second outlet 232 to which a hose 300 (see FIG. 4 and the like) is connected in the first use state is provided in the remaining portion of the upper surface 211 of the second housing 210.

The third inlet 221 is provided in the rear portion of the attachment surface 212. An opening 212a is provided at the front side of the attachment surface 212. More specifically, the opening 212a is provided between the step portion 215 and the attachment surface 212. The opening 212a is provided to open vertically upward.

The first inlet 231 and the third outlet 222 are provided to face the opening 212a in the second housing 210.

The opening 212a is closed by the rotating body 280 in the first use state. In the state that the opening 212a is closed by the rotating body 280, the first inlet 231 and the first coupling path 282 are coupled to each other, and the third outlet 222 and a second coupling path 284 of the rotating body 280 described later are coupled to each other.

The second housing 210 supports the rotating body 280 in a rotatable manner. Specifically, the second housing 210 includes a pair of support portions 245, and the rotating body 280 is supported by the pair of support portions 245 in a rotatable manner. The pair of support portions 245 are provided to protrude upward from the upper ends of the pair of side peripheral surfaces facing each other in the lateral direction of the second housing 210.

The rotating body 280 has a substantially block shape. The rotating body 280 is provided with a shaft portion 285 protruding outward. The shaft portion 285 is pivotally supported by the pair of support portions 245. With this, the rotating body 280 is able to rotate around a rotation axis VL1. The rotation axis VL1 is parallel to the attachment surface 212. The rotation axis VL1 is parallel to the lateral direction of the second housing 210.

The rotating body 280 has the first coupling port 281 to which the first outlet 122 of the first housing 110 is detachably coupled in a direction intersecting the rotation axis VL1, and the first coupling path 282 communicating with the first coupling port 281.

The rotating body 280 has the second coupling port 283 to which the second inlet 121 of the first housing 110 is detachably coupled, and the second coupling path 284 communicating with the second coupling port 283.

The rotating body 280 is configured to rotate between a first position and a second position. In the first position, the first outlet 122 of the first housing 110 is coupled to the first coupling port 281 in a state that the first housing 110 and the second housing 210 are separated from each other. In the second position, the first housing 110 is attached to the second housing 210 by the rotation of the first housing 110 and the rotating body 280 as a single entity to approach the second housing 210 in a state that the first outlet 122 is coupled to the first coupling port 281.

In the first position, the first coupling port 281 and the second coupling port 283 of the rotating body 280 face upward. More specifically, in the first position, the central axis of the first coupling port 281 and the central axis of the second coupling port 283 are substantially parallel to the vertically upward direction.

In the second position, the first coupling port 281 and the second coupling port 283 face the rear side of the second housing 210. More specifically, in the second position, the central axis of the first coupling port 281 and the central axis of the second coupling port 283 are parallel to the attachment surface 212 and substantially parallel to the longitudinal direction of the second housing 210.

In the first position, the opening end of the first coupling path 282 and the opening end of the second coupling path 284 face the rear side of the second housing 210. More specifically, in the first position, the central axis of the opening end of the first coupling path 282 and the central axis of the opening end of the second coupling path 284 are parallel to the attachment surface 212 and substantially parallel to the longitudinal direction of the second housing 210.

In the second position, the opening end of the first coupling path 282 and the opening end of the second coupling path 284 face downward. More specifically, in the second position, the central axis of the opening end of the first coupling path 282 and the central axis of the opening end of the second coupling path 284 are substantially parallel to the vertically downward direction.

A damper 295 is provided for the shaft portion 285 described above. The damper 295 is made of a torsion coil spring, for example. The damper 295 buffers an impact when the rotating body 280 to which the main unit 100 is coupled moves from the first position to the second position.

The second housing 210 is provided with a first ancillary portion 291 and a second ancillary portion 292 that assist the attachment of the first housing 110 to the second housing 210, when the rotating body 280 moves to the second position in a state that the first outlet 122 is coupled to the first coupling port 281.

Two of the first ancillary portions 291 are provided. The two first ancillary portions 291 are provided at the both ends of the attachment surface 212 in the lateral direction of the second housing 210. The two first ancillary portions 291 are provided in the rear portion of the attachment surface 212.

An inclined portion 291a is provided at an upper end of the first ancillary portion 291. The inclined portion 291a is inclined downward toward the front side.

The two first ancillary portions 291 are fitted into the cutout portions 116 provided at the pair of side surfaces 115 of the first housing 110. The inclined portion 291a presses the inclined portion 116a forward when the rotating body 280 moves toward the second position in a state that the first outlet 122 is coupled to the first coupling port 281. With this, the first housing 110 may be pushed toward the rotating body 280, and the main unit 100 may reliably be coupled to the rotating body 280.

The second ancillary portion 292 is provided at a substantially central portion in the lateral direction in the rear portion of the attachment surface 212. The second ancillary portion 292 determines the position of the rear surface 114 of the first housing 110 when the rotating body 280 moves toward the second position in a state that the first outlet 122 is coupled to the first coupling port 281.

A locking claw 292a as the engaging portion that engages with the first housing 110 is provided at the upper end of the second ancillary portion 292. The locking claw 292a generates sound when engaging with the portion to be engaged (not illustrated) provided in a portion of the rear surface of the first housing 110. With this, it is possible for a user to confirm that the first housing 110 has been attached to the predetermined position on the attachment surface 212.

Note that the attached state that the first housing 110 is attached to the attachment surface 212 refers to the state that the lower surface 112 of the first housing 110 and the attachment surface 212 of the second housing face each other. That is, in the attached state, the lower surface 112 of the first housing 110 may or may not be in direct contact with the attachment surface 212 of the second housing 210. In a case that the lower surface 112 of the first housing 110 is not in direct contact with the attachment surface 212 of the second housing 210, another member such as a cushion may be interposed between the lower surface 112 of the first housing 110 and the second housing 210.

Figure 4:
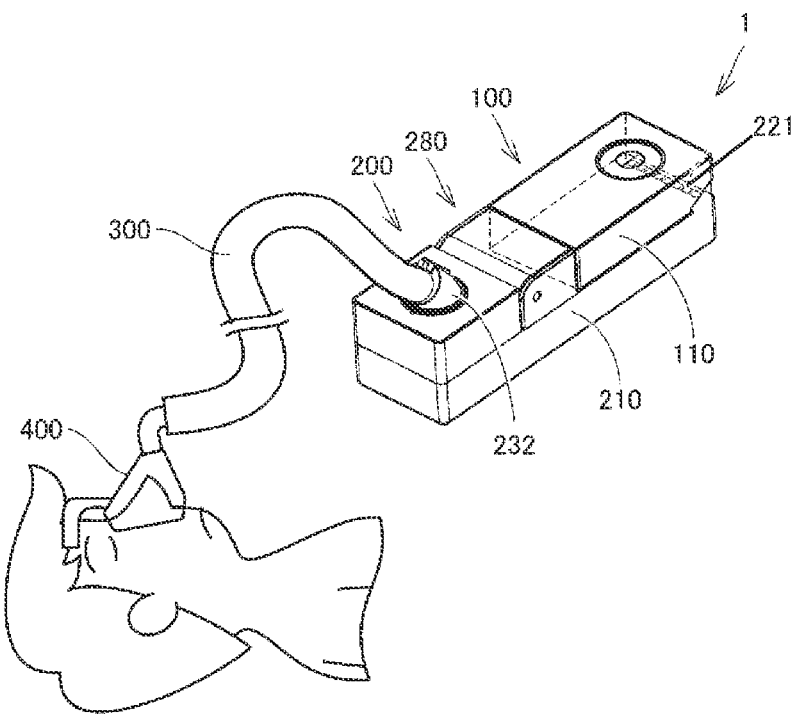
FIG. 4 is a diagram schematically illustrating a first use state of the CPAP device according to Embodiment 1.

FIG. 4 is a diagram schematically illustrating the first use state of the CPAP device according to Embodiment 1. The first use state of the CPAP device according to Embodiment 1 will be described with reference to FIG. 4.

As illustrated in FIG. 4, in the first use state, the CPAP device 1 is used in a state that the main unit 100 is attached to the base unit 200 as described above. In this case, one end of the hose 300 is coupled to the second outlet 232 provided in the base unit 200, and a mask 400 is coupled to the other end of the hose 300.

In the first use state, when the blower 140 provided in the main unit 100 is driven, air from the first outlet 122 provided in the main unit 100 goes through the rotating body 280, and is discharged to the outside of the CPAP device 1 from the second outlet 232 of the second housing 210. With this, the air discharged from the second outlet 232 is sent to the user's respiratory passage via the hose 300 and the mask 400.

Figure 5:
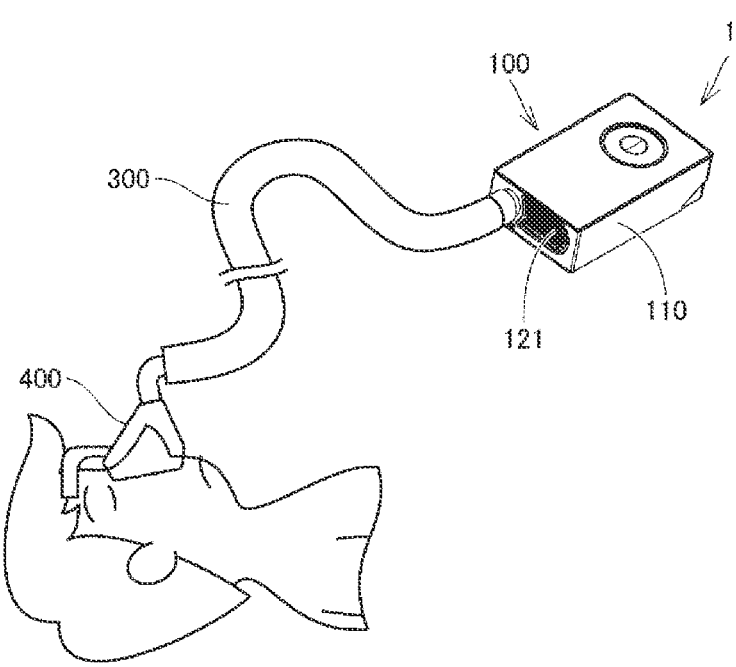
FIG. 5 is a diagram schematically illustrating a second use state of the CPAP device according to Embodiment 1.

FIG. 5 is a diagram schematically illustrating the second use state of the CPAP device according to Embodiment 1. The second use state of the CPAP device according to Embodiment 1 will be described with reference to FIG. 5.

As illustrated in FIG. 5, in the second use state, the CPAP device 1 is used in a state that the main unit 100 is not attached to the base unit 200 as described above. In this case, one end of the hose 300 is coupled to the first outlet 122 provided in the main unit 100, and the mask 400 is coupled to the other end of the hose 300.

In the second use state, when the blower 140 provided in the main unit 100 is driven, air is sucked into the CPAP device 1 from the second inlet 121 provided in the main unit 100, and the sucked air is discharged to the outside of the CPAP device 1 from the first outlet 122 provided in the main unit 100. With this, the air discharged from the first outlet 122 is sent to the user's respiratory passage via the hose 300 and the mask 400.

Here, the mask 400 is applied and worn to cover the nose or mouth of the user, for example. Note that the mask 400 having a shape and a structure suitable for the user may be selected from the various types of masks, and the shape and the structure illustrated in FIG. 4 are merely an example.

The CPAP device 1 widens the respiratory passage by continuously supplying air to the respiratory passage while adjusting the timing of the air supply to the timing of breathing of the user in order to prevent apnea during sleep. In the CPAP device 1, therefore, in both of the first use state and the second use state described above, various types of control are performed by the controller 130 (see FIG. 6) described later. The various types of control include feedback control, feedforward control, and the like, for example, based on a flow rate, pressure, and the like detected by a flow rate sensor 133 and a pressure sensor 134 (see FIG. 6) described later. With this, the number of revolutions of the blower 140 is increased or decreased to adjust, for example, the amount of air to be sent, thereby preventing the user from falling into apnea during sleep.

Figure 6:
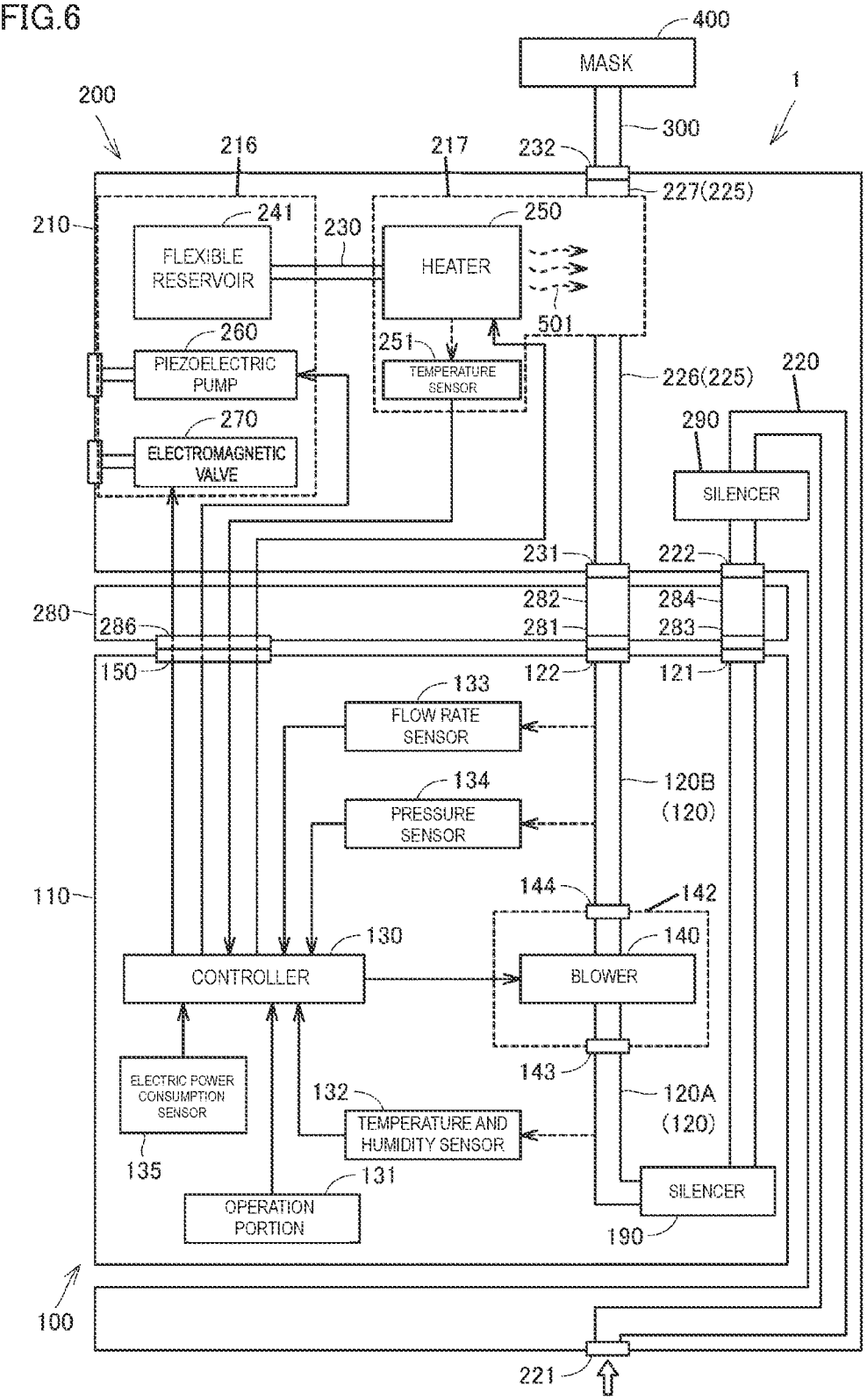
FIG. 6 is a diagram illustrating a configuration of functional blocks in the first use state of the CPAP device according to Embodiment 1.

FIG. 6 is a diagram illustrating the configuration of functional blocks in the first use state of the CPAP device according to Embodiment 1. With reference to FIG. 6, the configuration of functional blocks in the first use state of the CPAP device 1 according to Embodiment 1 will be described.

As illustrated in FIG. 6, the CPAP device 1 includes the controller 130, the operation portion 131, a temperature and humidity sensor 132, the flow rate sensor 133, the pressure sensor 134, an electric power consumption sensor 135, the blower 140, a silencer 190, a flexible reservoir 241, a heater 250, a temperature sensor 251, a piezoelectric pump 260, an electromagnetic valve 270, and a silencer 290.

Among them, the controller 130, the operation portion 131, the temperature and humidity sensor 132, the flow rate sensor 133, the pressure sensor 134, the electric power consumption sensor 135, the blower 140, and the silencer 190 are provided in the main unit 100. The flexible reservoir 241 is housed in a pressurizing chamber 216 provided in the base unit 200. The heater 250, the temperature sensor 251, the piezoelectric pump 260, the electromagnetic valve 270, and the silencer 290 are provided in the base unit 200. The base unit 200 is also provided with a water supply path 230.

In addition to the second inlet 121 and the first outlet 122 described above, a first flow path 120 is provided in the first housing 110. The first flow path 120 connects the second inlet 121 and the first outlet 122.

The blower 140 is provided in the first flow path 120. The blower 140 is made of a centrifugal fan, for example. The blower 140 is disposed in a blower chamber provided in the first housing 110, thereby being disposed in the first flow path 120.

Here, the blower 140 has a casing 142, and a suction port 143 and a discharging port 144 of the blower 140 are provided in the casing 142. The first flow path 120, therefore, includes an upstream flow path portion 120A connecting the second inlet 121 and the suction port 143, and a downstream flow path portion 120B connecting the discharging port 144 and the first outlet 122.

The silencer 190 may be provided in the upstream flow path portion 120A, which is the portion of the first flow path 120 positioned between the second inlet 121 and the suction port 143. The silencer 190 reduces leakage of noise generated by the blower 140 (such as operation sound of a drive motor included in the blower 140 or wind noise) to the outside via the second inlet 121.

The second housing 210 is provided with a humidification flow path 225 in addition to the first inlet 231 and the second outlet 232 described above. The humidification flow path 225 connects the first inlet 231 and the second outlet 232.

In the humidification flow path 225, air passing through the humidification flow path 225 is humidified by a humidification mechanism. With this, in the first use state, an appropriate amount of moisture 501 is given as a minute liquid to the air to be sent toward the respiratory passage of the user. Note that the humidification mechanism is mainly made of the flexible reservoir 241, the water supply path 230 described later, and the heater 250.

The humidification flow path 225 includes a flow path 226 connecting the first inlet 231 and a mixing chamber 217, and a flow path 227 connecting the second outlet 232 and the mixing chamber 217. That is, the first inlet 231 is connected to the mixing chamber 217 via the flow path 226 from upstream in the blowing direction. The second outlet 232 is connected to the mixing chamber 217 from downstream in the blowing direction via the flow path 227.

The first inlet 231 may be directly connected to the mixing chamber 217. Similarly, the second outlet 232 may be directly connected to the mixing chamber 217.

Further, the second housing 210 is provided with the second flow path 220 in addition to the third inlet 221 and the third outlet 222. The second flow path 220 connects the third inlet 221 and the third outlet 222. The silencer 290 is provided in the second flow path 220.

The silencer 290 reduces leakage of noise generated by the blower 140 (such as operation sound of a drive motor provided in the blower 140 or wind noise) to the outside via the second flow path 220 and the third inlet 221.

As described above, the water supply path 230 is provided in the base unit 200. The water supply path 230 connects the flexible reservoir 241 and the heater 250 serving as a vaporizer. The water supply path 230 delivers water stored in the flexible reservoir 241 to the heater 250. The flexible reservoir 241 is formed of a bag-shaped member that stores water therein, and is detachably coupled to the water supply path 230.

The heater 250 vaporizes the supplied water by heating, whereas the piezoelectric pump 260 is an air pump that pressure-feeds air. The piezoelectric pump 260 pressurizes the pressurizing chamber 216. The electromagnetic valve 270 discharges the air in the pressurizing chamber 216 to the outside of the base unit 200 to depressurize the pressurizing chamber 216.

The controller 130 includes, as main components, a central processing unit (CPU) that executes programs; a read only memory (ROM)/random access memory (RAM); driving units that drive the blower 140, the heater 250, the piezoelectric pump 260, and the electromagnetic valve 270; and an arithmetic unit that performs various arithmetic operations based on various information inputted from the temperature and humidity sensor 132, the flow rate sensor 133, the pressure sensor 134, the electric power consumption sensor 135, and the temperature sensor 251. The ROM/RAM includes a ROM that stores data in a nonvolatile manner, and a RAM that stores data generated through the execution of the programs by the CPU or data inputted via the operation portion 131 in a volatile manner. The constituents of the controller 130 are connected to each other via a data bus.

The processing in the CPU is achieved by pieces of hardware and software executed by the CPU. Such software is stored in the ROM/RAM in advance. The reception of an operation via the operation portion 131; the control of the drive motor that drives the blower 140, the heater 250, the piezoelectric pump 260, and the electromagnetic valve 270; and the various arithmetic operations described above are also achieved by software.

Electric power is supplied to the controller 130, the blower 140, the heater 250, the piezoelectric pump 260, the electromagnetic valve 270, and the like by an internal electric power source (not illustrated) or an external electric power supply (not illustrated). For example, an alternating current (AC) adapter or the like (not illustrated) is used for coupling to an external electric power supply.

The controller 130 is connected to the second terminal 150 provided in the first housing 110. The heater 250, the temperature sensor 251, the piezoelectric pump 260, and the electromagnetic valve 270 are connected to the first terminal 286 of the rotating body 280. As described above, in the first use state, the first terminal 286 and the second terminal 150 are coupled to each other, and this makes it possible for the controller 130 to control the heater 250, the temperature sensor 251, the piezoelectric pump 260, and the electromagnetic valve 270 provided in the base unit 200.

The temperature and humidity sensor 132 measures the temperature and humidity of the air introduced into the first flow path 120 by the blower 140. The temperature and humidity sensor 132 is provided in the upstream flow path portion 120A. The temperature and humidity of the air detected by the temperature and humidity sensor 132 are outputted to the controller 130 and mainly used for the humidifying operation by the humidification mechanism.

The flow rate sensor 133 measures the flow rate of the air between the CPAP device 1 and the hose 300. The pressure sensor 134 measures the pressure of the air sent out by the blower 140. The flow rate sensor 133 and the pressure sensor 134 correspond to a respiratory state detector, and are provided in the downstream flow path portion 120B.

The flow rate and the pressure detected by the flow rate sensor 133 and the pressure sensor 134 are outputted to the controller 130, and the controller 130 performs control such as feedback control or feedforward control, for example, based on the flow rate and the pressure. With this, the number of revolutions of the blower 140 is increased or decreased. Further, the flow rate and the pressure of the air detected by the flow rate sensor 133 and the pressure sensor 134 are also used for the humidifying operation by the humidification mechanism.

The electric power consumption sensor 135 measures the electric power supplied to the heater 250. The electric power consumption sensor 135 is made of an electric current monitor or the like, for example. The electric power consumption detected by the electric power consumption sensor 135 is outputted to the controller 130 and is mainly used for the humidifying operation by the humidification mechanism.

The temperature sensor 251 measures the temperature of the heater 250. The temperature sensor 251 is adjacent to the heater 250 in the second housing 210. The temperature of the heater 250 detected by the temperature sensor 251 is outputted to the controller 130 and is mainly used for the humidifying operation by the humidification mechanism.

Note that the CPAP device 1 may be provided with a display unit made of a liquid crystal display (LCD), an organic electro-luminescence (EL) display, or the like, in addition. Here, the display unit may be provided in the main unit 100 or in the base unit 200. The operation portion 131 does not need to be a button having a physical shape as illustrated in FIG. 1 and FIG. 3, and may be a touch screen or the like provided on a display surface of an LCD, for example. In the operation portion 131, buttons other than the button for switching ON/OFF of the electric power supply of the CPAP device 1 may be provided in the base unit 200.

Here, in the first use state, the rotating body 280 is positioned at the second position in a state of being coupled to the main unit 100, as described above. With this, the first outlet 122 of the first housing 110 and the first inlet 231 of the second housing 210 are coupled to each other by the first coupling port 281 and the first coupling path 282 of the rotating body 280. Similarly, the second inlet 121 of the first housing 110 and the third outlet 222 of the second housing 210 are coupled to each other by the second coupling port 283 and the second coupling path 284 of the rotating body 280.

With this, in the first use state, when the blower 140 is driven, the air sucked from the third inlet 221 is discharged from the second outlet 232 via the second flow path 220, the second coupling path 284, the first flow path 120, the first coupling path 282, and the humidification flow path 225 in this order. The air discharged from the second outlet 232 is, then, sent to the user's respiratory passage via the hose 300 and the mask 400.

Figure 7:
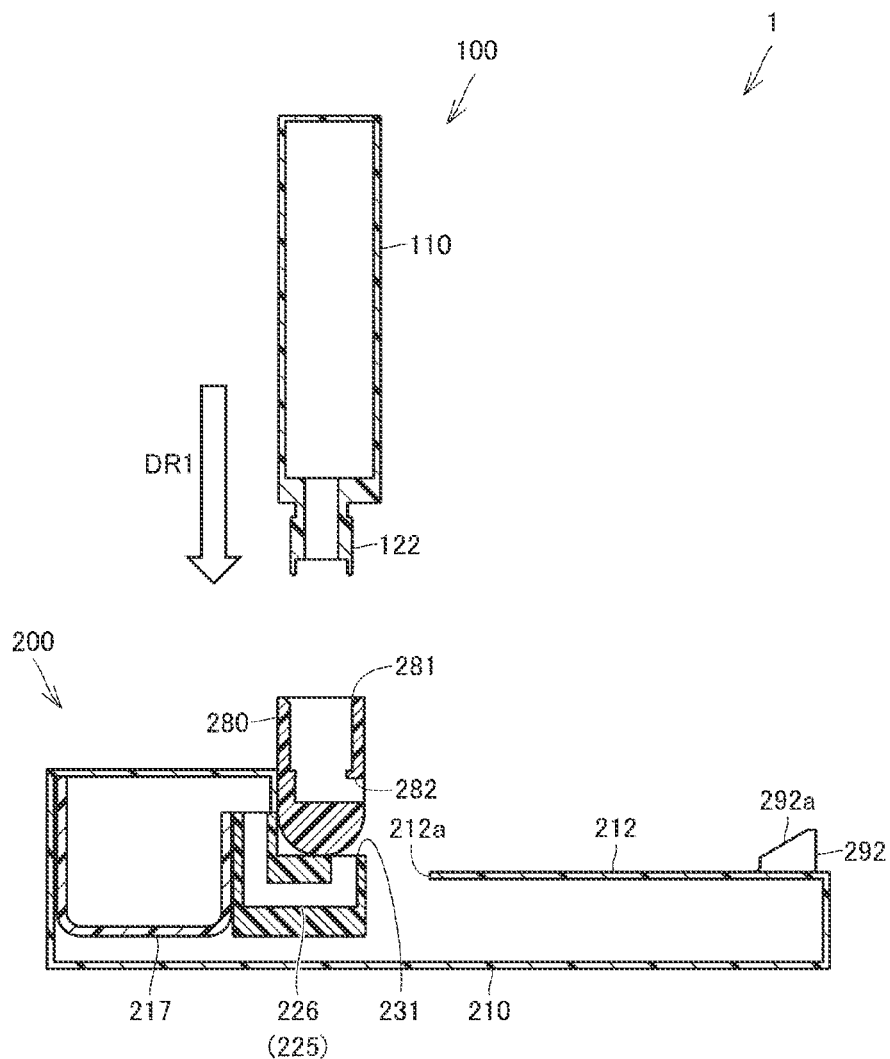
FIG. 7 is a sectional view illustrating a first operation when the main unit is attached to the base unit in the CPAP device according to Embodiment 1.
Figure 8:
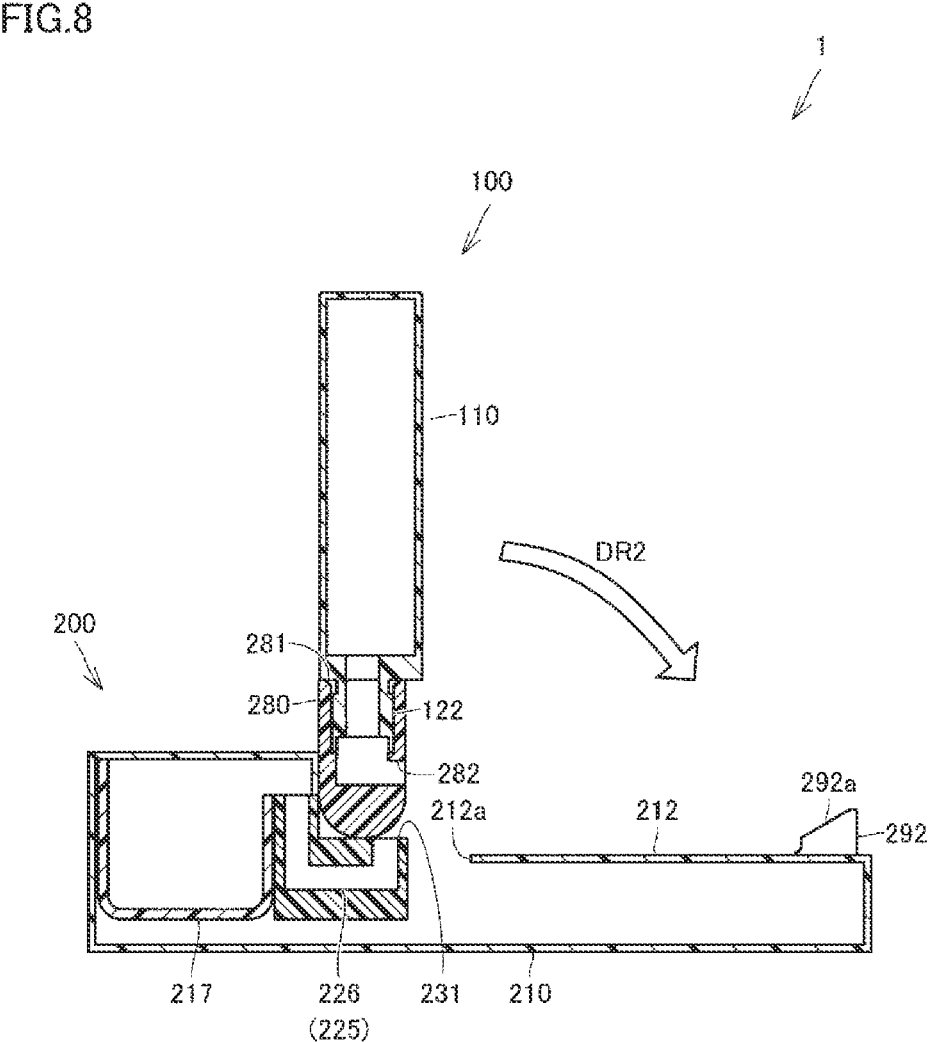
FIG. 8 is a sectional view illustrating a second operation when the main unit is attached to the base unit in the CPAP device according to Embodiment 1.
Figure 9:
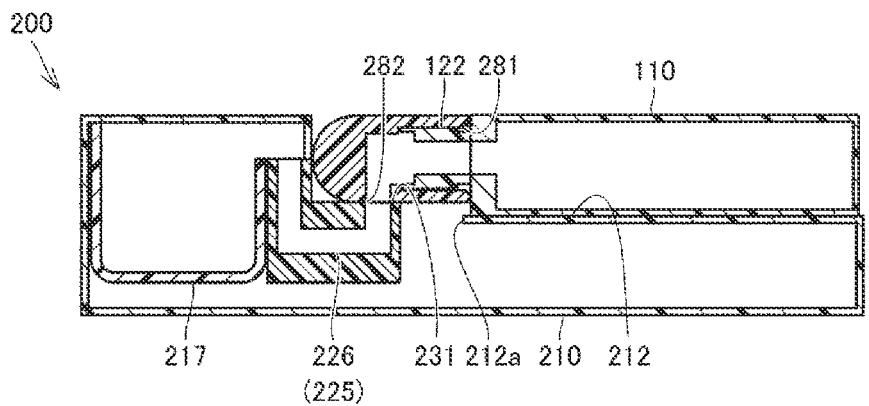
FIG. 9 is a sectional view illustrating a state that the main unit is attached to the base unit in the CPAP device according to Embodiment 1.

FIG. 7 and FIG. 8 are sectional views illustrating a first operation and a second operation when the main unit is attached to the base unit in the CPAP device according to Embodiment 1. FIG. 9 is a sectional view illustrating a state that the main unit is attached to the base unit in the CPAP device according to Embodiment 1. An operation of attaching the main unit 100 to the base unit 200 will be described with reference to FIG. 7 to FIG. 9.

As illustrated in FIG. 7, in a state before the main unit 100 is attached to the base unit 200, the rotating body 280 is positioned at the first position, and the first coupling port 281 of the rotating body 280 faces in a direction intersecting the rotation axis of the rotating body 280. With this, the first outlet 122 of the main unit 100 is easily coupled to the first coupling port 281.

When the main unit 100 is coupled to the rotating body 280, the user holds the main unit 100 with one hand so that the first outlet 122 faces the first coupling port 281. Subsequently, the first outlet 122 is coupled to the first coupling port 281. As described above, in the first position, the first outlet 122 is coupled to the first coupling port 281 in a state that the first housing 110 is separated from the second housing 210.

In Embodiment 1, the first coupling port 281 faces upward (more specifically, vertically upward). With this, as indicated by the direction of an arrow DR1 in FIG. 7, moving the main unit 100 held by one hand downward (more specifically, vertically downward) makes the first outlet 122 be coupled to the first coupling port 281.

In this case, moving the main unit 100 downward makes it possible to stably and easily push the first outlet 122 into the first coupling port 281. Further, the first outlet 122 may be coupled to the first coupling port 281 by using the weight of the main unit 100. With this, the first outlet 122 may reliably be coupled to the first coupling port 281. Coupling the first outlet 122 to the first coupling port 281 makes the main unit 100 be coupled to the rotating body 280.

Although not illustrated in FIG. 7, coupling the first outlet 122 to the first coupling port 281 makes the second inlet 121 be also coupled to the second coupling port 283. Further, the second terminal 150 is coupled to the first terminal 286.

Subsequently, as indicated by an arrow DR2 in FIG. 8, in a state that the first outlet 122 is coupled to the first coupling port 281, the rotating body 280 is rotated such that the first housing 110 approaches the second housing 210. With this, the rotating body 280 rotates to the second position.

As illustrated in FIG. 9, when the rotating body 280 rotates to the second position, the main unit 100 and the rotating body 280 rotate as a single entity, and the first housing 110 is attached to the attachment surface 212 of the second housing 210. At this time, the opening 212a positioned at the front side of the attachment surface 212 is closed by the rotating body 280. Further, the first outlet 122 and the first inlet 231 are coupled by the first coupling port 281 and the first coupling path 282 of the rotating body 280. Similarly, although not illustrated in FIG. 9, the second inlet 121 and the third outlet 222 of the second housing 210 are coupled by the second coupling port 283 and the second coupling path 284 of the rotating body 280.

As described above, in the CPAP device 1 according to Embodiment 1, in a state that the first housing 110 and the second housing 210 are separated from each other, the first outlet 122 is coupled to the first coupling port 281 in the direction intersecting the rotation axis VL1, and the main unit 100 is coupled to the rotating body 280. With this, since the first outlet 122 may be coupled to the first coupling port 281 at a position where the second housing 210 does not interfere with the coupling, the main unit 100 may reliably be coupled to the rotating body 280. Further, rotating the rotating body 280 to a predetermined position such that the first housing 110 is attached to the second housing 210 makes it possible to couple the first outlet 122 and the first inlet 231, via the first coupling port 281 and the first coupling path 282 provided in the rotating body 280.

With this, in comparison with a case that the first outlet 122 of the first housing 110 is directly coupled to the first inlet 231 of the second housing 210, the user may couple the air blowing paths of the first housing 110 and the second housing 210 using the rotating body 280, without necessarily worrying about how much force is suitable for coupling the first outlet 122, and how much distance is suitable for coupling the first outlet 122. As a result, it is possible to reliably couple the main unit 100 and the base unit 200.

Further, when the first housing 110 is attached to the attachment surface 212 of the second housing 210 by rotating the rotating body 280 to the second position in a state that the first outlet 122 is coupled to the first coupling port 281, pressing the first housing 110 toward the rotating body 280 by the first ancillary portion 291, as described above, makes it possible to more reliably couple the main unit 100 and the rotating body 280.

Embodiment 2

Figure 10:
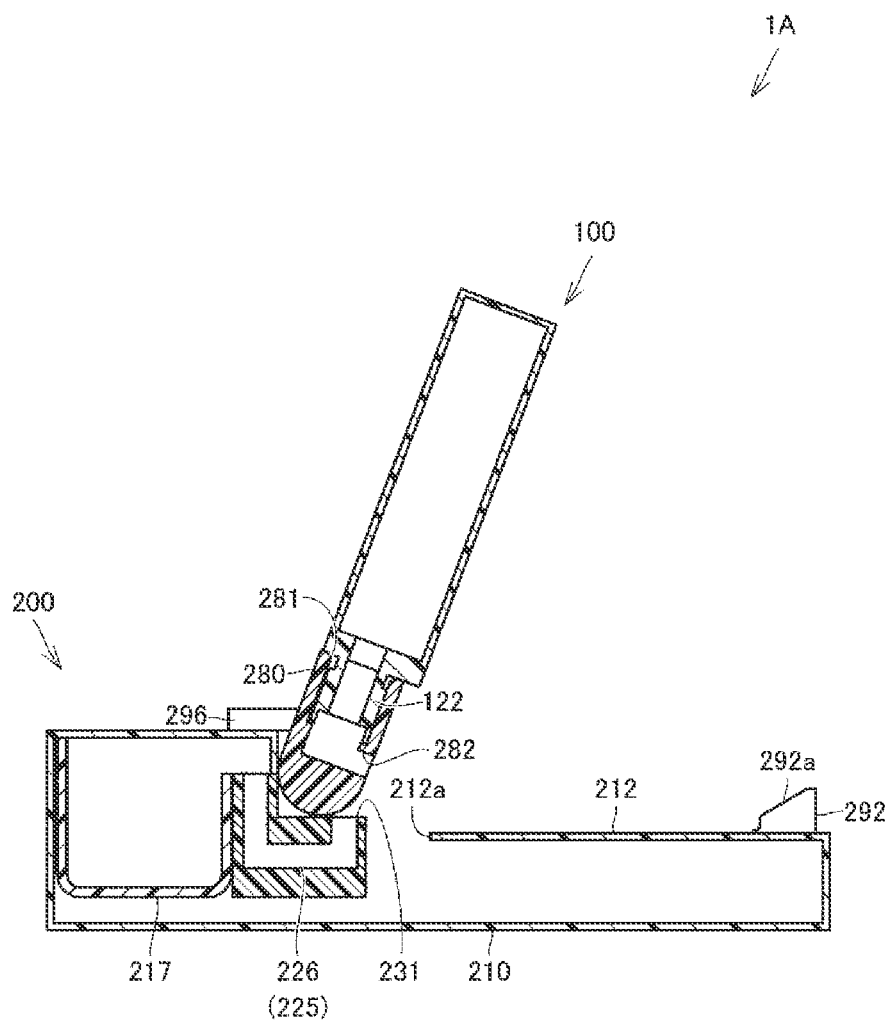
FIG. 10 is a sectional view illustrating a state that the main unit is coupled to a rotating body in the CPAP device according to Embodiment 2.

FIG. 10 is a sectional view illustrating a state that the main unit is coupled to a rotating body in the CPAP device according to Embodiment 2. A CPAP device 1A according to Embodiment 2 will be described with reference to FIG. 10.

As illustrated in FIG. 10, the CPAP device 1A according to Embodiment 2, when compared with the CPAP device 1 according to Embodiment 1, is different in that the rotating body 280 is configured to rotate by the own weight of the main unit 100 when moving from the first position to the second position. Other configurations are substantially the same.

In Embodiment 2, the base unit 200 is provided with a stopper 296 that determines the posture of the rotating body 280 in the first position. In the first position, the stopper 296 determines the posture of the rotating body 280 such that the first coupling port 281 faces obliquely upward at a predetermined angle. Note that, the predetermined angle is, as described above, an angle that allows the rotating body 280 to rotate to the second position by the own weight of the main unit 100 when the main unit 100 is coupled to the rotating body 280 in the first position.

Even with such a configuration, the CPAP device 1A according to Embodiment 2 may obtain substantially the same effects as those of the CPAP device 1 according to Embodiment 1. In addition, since the rotating body 280 moves from the first position to the second position by the own weight of the main unit 100 coupled to the rotating body 280, it is possible for the user to save the action of rotating the rotating body 280. With this, the convenience of the CPAP device 1A may be improved.

Note that, in Embodiment 1 described above, a case that the rotation axis VL1 of the rotating body 280 is parallel to the attachment surface 212 of the second housing 210 has been exemplified and described. However, the configuration is not limited thereto, and the rotation axis VL1 may be perpendicular to the attachment surface 212.

In this case, the first outlet 122 is coupled to the first coupling port 281 in a lateral direction in a state that the first housing 110 and the second housing 210 are separated from each other. In this state, rotating the first housing 110 and the rotating body 280 as a single entity to approach the second housing 210 makes the first housing 110 be attached to the attachment surface 212 of the second housing 210. Coupling the main unit 100 to the rotating body 280 makes it possible that the main unit 100 is guided to a predetermined position by the rotating body 280.

The embodiments disclosed herein are illustrative in all respects and are not restrictive. The scope of the present disclosure is indicated by the claims, and includes all modifications within the meaning and range of equivalency of the claims.

REFERENCE SIGNS LIST 1, 1A CPAP DEVICE, 100 MAIN UNIT, 110 FIRST HOUSING, 111 UPPER SURFACE, 112 LOWER SURFACE, 113 FRONT SURFACE, 114 REAR SURFACE, 115 SIDE SURFACE, 116 CUTOUT PORTION, 116a INCLINED PORTION, 120 FIRST FLOW PATH, 120A UPSTREAM FLOW PATH PORTION, 120B DOWNSTREAM FLOW PATH PORTION, 121 SECOND INLET, 122 FIRST OUTLET, 130 CONTROLLER, 131 OPERATION PORTION, 132 TEMPERATURE AND HUMIDITY SENSOR, 133 FLOW RATE SENSOR, 134 PRESSURE SENSOR, 135 ELECTRIC POWER CONSUMPTION SENSOR, 140 BLOWER, 142 CASING, 143 SUCTION PORT, 144 DISCHARGING PORT, 150 SECOND TERMINAL, 190 SILENCER, 200 BASE UNIT, 210 SECOND HOUSING, 211 UPPER SURFACE, 212 ATTACHMENT SURFACE, 212a OPENING, 215 STEP PORTION, 216 PRESSURIZING CHAMBER, 217 MIXING CHAMBER, 220 SECOND FLOW PATH, 221 THIRD INLET, 222 THIRD OUTLET, 225 HUMIDIFICATION FLOW PATH, 226, 227 FLOW PATH, 230 WATER SUPPLY PATH, 231 FIRST INLET, 232 SECOND OUTLET, 241 FLEXIBLE RESERVOIR, 245 SUPPORT PORTION, 250 HEATER, 251 TEMPERATURE SENSOR, 260 PIEZOELECTRIC PUMP, 270 ELECTROMAGNETIC VALVE, 280 ROTATING BODY, 281 FIRST COUPLING PORT, 282 FIRST COUPLING PATH, 283 SECOND COUPLING PORT, 284 SECOND COUPLING PATH, 285 SHAFT PORTION, 286 FIRST TERMINAL, 290 SILENCER, 291 FIRST ANCILLARY PORTION, 291a INCLINED PORTION, 292 SECOND ANCILLARY PORTION, 292a LOCKING CLAW, 295 DAMPER, 296 STOPPER, 300 HOSE, 400 MASK, 501 MOISTURE

The invention claimed is:

1. A respiratory blowing device, comprising:
a first unit including a blower and a first housing that houses the blower; and
a second unit including a rotating body to which the first unit is detachably coupled and a second housing that rotatably supports the rotating body, wherein
the first housing is configured to be attached to the second housing,
the first housing includes a first outlet for discharging air to an outside of the first housing,
the rotating body includes a first coupling port to which the first outlet is detachably coupled in a direction intersecting a rotation axis of the rotating body, and a first coupling path communicating with the first coupling port,
the second housing includes a first inlet configured to be coupled to the first coupling path and to which air is introduced from the first coupling path, and a second outlet for discharging air introduced from the first inlet to an outside of the second housing, and
the rotating body is configured to rotate between a first position where the first outlet is coupled to the first coupling port while the first housing and the second housing are separated from each other, and a second position where the first housing is attached to the second housing by rotation of the first housing to approach the second housing so that the first outlet is coupled to the first coupling port.

2. The respiratory blowing device according to claim 1, wherein
the second housing comprises an ancillary portion that assists attachment of the first housing to the second housing when the rotating body moves to the second position so that the first outlet is coupled to the first coupling port.

3. The respiratory blowing device according to claim 2, wherein
the ancillary portion comprises an engaging portion that engages the first housing with the second housing so that the first housing is attached to the second housing.

4. The respiratory blowing device according to claim 1, wherein
the second housing has an attachment surface that faces vertically upward and to which the first housing is attached,
the rotation axis of the rotating body is parallel to the attachment surface, and
the first coupling port of the rotating body faces vertically upward in the first position.

5. The respiratory blowing device according to claim 1, wherein
the rotating body is configured to rotate to the second position by an own weight of the first unit so that the first outlet is coupled to the first coupling port in the first position.

6. The respiratory blowing device according to claim 1, wherein
the rotating body includes a first terminal,
the first housing includes a second terminal configured to be coupled to the first terminal, and
the second terminal is coupled to the first terminal so that the first outlet is coupled to the first coupling port.

7. The respiratory blowing device according to claim 1, wherein
the first housing includes a second inlet configured to introduce air from the outside of the first housing and a first flow path that connects the second inlet and the first outlet and that comprises the blower,
the second housing includes a third inlet configured to introduce air from the outside of the second housing, a third outlet configured to discharge air introduced from the third inlet to the outside of the second housing, and a second flow path connecting the third inlet and the third outlet,
a silencer is in the second flow path,
the rotating body includes a second coupling port to which the second inlet is detachably coupled and a second coupling path communicating with the second coupling port, and
the third outlet is configured to be coupled to the second coupling path.

8. The respiratory blowing device according to claim 1, further comprising:
a damper that buffers an impact when the rotating body to which the first unit is coupled moves from the first position to the second position.

9. The respiratory blowing device according to claim 1, wherein
the second housing has an attachment surface that faces vertically upward and to which the first housing is attached,
the rotation axis of the rotating body is parallel to the attachment surface, and
the first coupling port of the rotating body faces vertically upward in the first position.

10. The respiratory blowing device according to claim 2, wherein
the rotating body is configured to rotate to the second position by an own weight of the first unit so that the first outlet is coupled to the first coupling port in the first position.

11. The respiratory blowing device according to claim 3, wherein
the rotating body is configured to rotate to the second position by an own weight of the first unit so that the first outlet is coupled to the first coupling port in the first position.

12. The respiratory blowing device according to claim 4, wherein
the rotating body is configured to rotate to the second position by an own weight of the first unit so that the first outlet is coupled to the first coupling port in the first position.

13. The respiratory blowing device according to claim 2, wherein
the rotating body includes a first terminal,
the first housing includes a second terminal configured to be coupled to the first terminal, and
the second terminal is coupled to the first terminal so that the first outlet is coupled to the first coupling port.

14. The respiratory blowing device according to claim 3, wherein
the rotating body includes a first terminal,
the first housing includes a second terminal configured to be coupled to the first terminal, and
the second terminal is coupled to the first terminal so that the first outlet is coupled to the first coupling port.

15. The respiratory blowing device according to claim 4, wherein
the rotating body includes a first terminal,
the first housing includes a second terminal configured to be coupled to the first terminal, and
the second terminal is coupled to the first terminal so that the first outlet is coupled to the first coupling port.

16. The respiratory blowing device according to claim 5, wherein
the rotating body includes a first terminal,
the first housing includes a second terminal configured to be coupled to the first terminal, and
the second terminal is coupled to the first terminal so that the first outlet is coupled to the first coupling port.

17. The respiratory blowing device according to claim 2, wherein
the first housing includes a second inlet configured to introduce air from the outside of the first housing and a first flow path that connects the second inlet and the first outlet and that comprises the blower,
the second housing includes a third inlet configured to introduce air from the outside of the second housing, a third outlet configured to discharge air introduced from the third inlet to the outside of the second housing, and a second flow path connecting the third inlet and the third outlet,
a silencer is in the second flow path,
the rotating body includes a second coupling port to which the second inlet is detachably coupled and a second coupling path communicating with the second coupling port, and
the third outlet is configured to be coupled to the second coupling path.

18. The respiratory blowing device according to claim 3, wherein
the first housing includes a second inlet configured to introduce air from the outside of the first housing and a first flow path that connects the second inlet and the first outlet and that comprises the blower,
the second housing includes a third inlet configured to introduce air from the outside of the second housing, a third outlet configured to discharge air introduced from the third inlet to the outside of the second housing, and a second flow path connecting the third inlet and the third outlet,
a silencer is in the second flow path,
the rotating body includes a second coupling port to which the second inlet is detachably coupled and a second coupling path communicating with the second coupling port, and
the third outlet is configured to be coupled to the second coupling path.

19. The respiratory blowing device according to claim 4, wherein
the first housing includes a second inlet configured to introduce air from the outside of the first housing and a first flow path that connects the second inlet and the first outlet and that comprises the blower, the second housing includes a third inlet configured to introduce air from the outside of the second housing, a third outlet configured to discharge air introduced from the third inlet to the outside of the second housing, and a second flow path connecting the third inlet and the third outlet, a silencer is in the second flow path, the rotating body includes a second coupling port to which the second inlet is detachably coupled and a second coupling path communicating with the second coupling port, and the third outlet is configured to be coupled to the second coupling path.

20. The respiratory blowing device according to claim 5, wherein the first housing includes a second inlet configured to introduce air from the outside of the first housing and a first flow path that connects the second inlet and the first outlet and that comprises the blower, the second housing includes a third inlet configured to introduce air from the outside of the second housing, a third outlet configured to discharge air introduced from the third inlet to the outside of the second housing, and a second flow path connecting the third inlet and the third outlet, a silencer is in the second flow path, the rotating body includes a second coupling port to which the second inlet is detachably coupled and a second coupling path communicating with the second coupling port, and the third outlet is configured to be coupled to the second coupling path.

\* \* \* \* \*